(12) United States Patent
Jung

(10) Patent No.: US 8,058,399 B2
(45) Date of Patent: *Nov. 15, 2011

(54) MULTISPECIFIC REAGENT FOR SELECTIVELY STIMULATING CELL SURFACE RECEPTORS

(76) Inventor: Gundram Jung, Rottenburg-Wendelsheim (DE)

( * ) Notice: Subject to any disclaimer, the term of this patent is extended or adjusted under 35 U.S.C. 154(b) by 881 days.

This patent is subject to a terminal disclaimer.

(21) Appl. No.: 10/348,651

(22) Filed: Jan. 21, 2003

(65) Prior Publication Data

US 2003/0232049 A1    Dec. 18, 2003

Related U.S. Application Data

(63) Continuation of application No. PCT/EP01/08147, filed on Jul. 14, 2001.

(30) Foreign Application Priority Data

Jul. 20, 2000    (DE) .................................. 100 34 607

(51) Int. Cl.
*C07K 16/00* (2006.01)
*C07K 16/46* (2006.01)
(52) U.S. Cl. .................................. 530/387.1; 530/387.3
(58) Field of Classification Search .................. None
See application file for complete search history.

(56) References Cited

U.S. PATENT DOCUMENTS

| 5,891,434 A | * | 4/1999 | Krammer et al. | .......... | 424/143.1 |
| 6,010,902 A | | 1/2000 | Ledbetter et al. | | |
| 6,042,826 A | * | 3/2000 | Caligiuri et al. | .......... | 424/130.1 |

FOREIGN PATENT DOCUMENTS

| DE | 195 31 3849 A1 | 2/1997 |
| EP | 0 336 379 | 11/1989 |
| JP | 2000-503672 A | 3/2000 |
| WO | WO 94/20625 | 9/1994 |
| WO | WO 97/08205 | 3/1997 |
| WO | WO 97/12632 | * 4/1997 |
| WO | WO 98/04592 A1 | 2/1998 |
| WO | WO 99/48527 | 9/1999 |
| WO | WO 00/29431 | 5/2000 |

OTHER PUBLICATIONS

Jung et al. Target Cell-restricted Triggering of the CD95 (APO-1/Fas) Death Receptor with Bispecific Antibody Fragments. Cancer Research 61, 1846-1848, Mar. 1, 2001.*
Wahl et al. Improved radioimaging and tumor localization with monoclonal F(ab')2. J Nucl Med. Apr. 1983;24(4):316-325.*
Herrmann et al. Construction of optimized bispecific antibodies for selective activation of the death receptor CD95. Cancer Res. Feb. 15, 2008;68(4):1221-7.*
Jung et al. Monoclonal and Bispecific Antibodies as Novel Therapeutics. Apoptotic Pathways as Targets for Novel Therapies in Cancer and Other Diseases, Ed. Los and Gibson, Springer, pp. 229-242, 2005.*
Lens et al. A dual role for both CD40-ligand and TNF-alpha in controlling human B cell death. The Journal of Immunology, 156(2):507-514, 1996.*
Coney et al. (1994) "Apoptotic cell death induced by a mouse-human anti-apo-1 chimeric antibody leads to tumor regression" Int. J. Cancer 58:562-567.
Jung et al. (1991) "Target cell-induced T cell activation with bi- and trispecific antibody fragments" Eur. J. Immunol. 21:2431-5 (Abstract Only).
Lexikon der Biologie/ Encyclopaedia of Biology 1999, pp. 323-329.
Roosnek et al. (1990) "T cell activation by a bispecific anti-CD3/anti-major histocompatibliity complex class I antibody" Eur. J. Immunol. 20:1393-6 (Abstract Only).
Segal et al. (1999) "Bispecific antibodies in cancer therapy" Current Opinion in Immunology 11:558-562.
Ogasawara, J. et al. (1993) "Lethal effect of the anti-Fas antibody in mice" *Nature* 364:806-809.
Pfosser, A. et al. (1999) "Role of target antigen in bispecific-antibody-mediated killing of human gliobastoma cells: a pre-clinical study" *Int. J. Cancer* 80:612-616.
Trauth, B. et al. (1989) "Monoclonal antibody-mediated tumor regression by induction of apoptosis" *Science* 245:301-305.
Pitti, R.M. (1996) Induction of apoptosis by Apo-2 Ligand, a new member of the tumor necrosis factor cytokine family *J. Biol. Chem.* 271:12687-12690.
Ashkenazi, a. et al., Safety and Antitumor Activity of Recombinant Soluable Apo2 Ligand. *The Journal of Clinical Investigation*, 104:155-162, 1999.
Dhein, J. et al. 1992 Induction of Apoptosis by Monoclonal Antibody Anti-Apo-1 Class Switch Variants is Dependent on Cross-Linking of Apo-1 Cell Surface Antigens, *The Journal of Immunology*, 149:3166-3173.
Emmrich, F. et al. 1988 Selective Stimulation of Human T Lymphocyte Subsets by Heteroconjugates of Antibodies to the T Cell Receptor and to Subset—Specific Differentiation Antigens, *European Journal of Immunology*, 18:645-648.
Griffith, T. et al. 1999, Functional Analysis of TRAIL Receptors Using Monoclonal Antibodies, *The Journal of Immunology* 162:2597-2605.

* cited by examiner

*Primary Examiner* — Maher Haddad
(74) *Attorney, Agent, or Firm* — Knobbe Martens Olson & Bear LLP

(57) ABSTRACT

A multispecific reagent has at least one first binding site for a cell surface receptor which requires multimeric ligand binding to be stimulated. The reagent possesses a second binding site for a target antigen which is expressed on the same cell as the cell surface receptor.

2 Claims, 3 Drawing Sheets

MULTISPECIFIC REAGENT FOR SELECTIVELY STIMULATING CELL SURFACE RECEPTORS

RELATED APPLICATION

This is a continuation application of International Patent Application PCT/EP01/08147, filed Jul. 14, 2001, designating the United States, and published in German as WO 02/08291 A2, which claims priority to German application number 100 34 607, filed Jul. 20, 2000.

BACKGROUND OF THE INVENTION

1. Field of the Invention

The present invention is concerned, in a general manner, with stimulating cells and in particular with selectively activating receptors on the cell surface.

2. Description of the Related Art

It is well known that extracellular signals are transmitted through the plasma membrane by way of receptor proteins which are able to convert the extracellular binding of ligands into an intracellular biochemical event. In this way, cell surface receptors activate intracellular signal pathways which lead to different sites in the cell and induce particular events at these sites.

All cell surface receptors are transmembrane proteins or protein complexes which establish a connection between the inside and the outside of the cell. Many receptors undergo a defined change in the protein conformation when their respective ligand is bound. In the case of some receptor types, this change in conformation leads to an ion channel being opened while, in the case of other receptors, the change in conformation leads to the cytoplasmic region of the receptor being affected in such a way that it can associate with intracellular signal proteins and signal enzymes and activate these proteins and enzymes.

A crucial effect of ligands being bound to receptors is frequently that of multimerizing or crosslinking the receptor and thereby activating the intracellular signal cascade. Such a crosslinking of surface receptors can either be effected by the physiological ligands of the receptors or, for example, be effected in vitro using appropriate crosslinking antibodies.

For example, it has been demonstrated, in the case of lymphocytes, that, while it is not possible to stimulate specific antigen receptors as a result of binding F(ab') fragments, which possess only one binding site, the receptors form clusters, and the cells are activated, as the result of binding $(Fab')_2$ antibody fragments, i.e. fragments possessing two binding sites. However, a stronger reaction is achieved if lymphocytes are stimulated by intact antibodies which are bound to cells which carry receptors for the immunoglobulin Fc moiety. In other words, activation takes place when receptors are efficiently crosslinked by being bound to many identical antibody molecules which are provided by other cells which possess Fc receptors for the constant regions of the intact antibodies. The receptors are efficiently crosslinked by the antibodies which are immobilized in this way.

In vitro, such a crosslinking can, on the one hand, be achieved by the constant regions of antibodies which are bound to the receptors being crosslinked by way of protein A or by way of other antibodies which bind specifically to the constant regions of the antibodies which are bound to the receptors.

For example, it is known that the members of the TNF (tumor necrosis factor) family act as trimers and that the ligand induced trimerization of their receptors is the critical event in initiating signal transmission.

Dhein et al., INDUCTION OF APOPTOSIS BY MONOCLONAL ANTIBODY ANTI-APO-1 CLASS SWITCH VARIANTS IS DEPENDENT ON CROSS-LINKING OF APO-1 CELL SURFACE ANTIGENS", the Journal of Immunology, volume 149, 1992, pages 3166-3173 report that efficient crosslinking of the APO-1 cell surface antigen leads to the induction of apoptosis. They show that, while apoptosis is induced in SKW6.4 cells when anti-APO-1 $F(ab')_2$ fragments which are crosslinked by way of a sheep anti-mouse antibody bind to the APO-1 receptor, the binding of the $F(ab')_2$ fragments on their own is insufficient to achieve this. The authors conclude from these results that the bivalency of the antibody, which thus possesses two binding sites for the APO-1 cell surface antigen, is insufficient for inducing apoptosis and that, on the contrary, efficient crosslinking of the APO-1 cell surface antigen is necessary in order to achieve this.

The sequence of the APO-1 antigen, and a monoclonal antibody directed against the APO-1 antigen are described in U.S. Pat. No. 5,891,434. This patent specification mentions that the anti-APO-1 antibodies can be used for treating tumors which the APO-1 antigen, with it furthermore being possible to induce apoptosis in different types of cells.

However, it is known that many cells in the body carry the APO 1 cell surface antigen, which means that administering an anti-APO-1 antibody to a tumor patient would lead not only to an attack on the tumor cells but also, in addition to this, to an attack on other, healthy and perhaps even essential cells which also carry the APO-1 surface antigen.

Against this background, the use of the known anti-APO-1 antibodies for treating tumor patients, for example, is only suitable under certain circumstances.

The TRAIL (TNF-related apoptosis-inducing ligand) receptors R1 and R2 represent another type of death receptor which is activated by crosslinking; see Griffith et al., "Functional Analysis of TRAIL Receptors using Monoclonal Antibodies", The Journal of Immunology, volume 162, 1999, pages 2597-2605. The authors report that, while all the anti-TRAIL-R2 antibodies, and two of the anti-TRAIL-R1 antibodies, were unable to induce any lysis, or only able to induce minimal lysis, of TRAIL-sensitive melanoma cells when they were added to the cells in solution, these antibodies exhibited an increase in their lytic ability when they were immobilized on a culture plate such that they were able to ensure that the TRAIL-R1 and TRAIL-R2 death receptors were crosslinked.

Antibodies against the death receptors TRAIL-R1 and TRAIL-R2 also act nonspecifically on TRAIL-sensitive cells, which means that they are only of slight therapeutic value.

In addition to this, it is known that what are termed bispecific antibodies, i.e. antibodies which possess a specificity for a tumor-associated antigen and a specificity for a surface antigen on defensive cells of the immune system, such as macrophages, T-lymphocytes or natural killer cells, which cells are activated by way of this binding, can be employed in cancer immunotherapy for directing the activity of the defensive cells toward the particular target cells.

In a general manner, bispecific antibodies are antibodies which are able to bind two different epitopes and are monovalent for each epitope. They are prepared by oxidizing monovalent F(ab') fragments to give an $F(ab')_2$ fragment, by fusing two hybridoma cell lines to give hybrid hybridoma or quadroma cells, or recombinantly.

Jung et al., "Target cell-induced T cell activation with bi- and trispecific antibody fragments", Eur. J. Immunol., volume 21, 1991, pages 2431-2435 describe the preparation of bispecific F(ab) hybrid fragments which are monovalent for each antigen. The reader is referred to this publication for further references to the preparation of bispecific antibodies.

The authors demonstrate that bispecific antibodies or fragments can be used to effect a target cell induced activation of T cells, by the antibodies on the one hand binding to the target antigen on the target cell and, on the other hand, binding to the CD3 and/or CD28 receptor on the T cell.

Segal et al., "Bispecific antibodies in cancer therapy", Current Opinion in Immunology, volume 11, 1999, pages 558-562 also describe the use of bispecific antibodies for directing an effector cell to a target cell which it would not otherwise recognize. For this purpose, the bispecific antibodies bind to a surface molecule on the target cell and to a surface receptor on the effector cell.

Roosnek et al., "T cell activation by a bispecific anti-CD3/anti-major histocompatibility complex class I antibody", Eur. J. Immunol., volume 20, 1990, pages 1393-1396 showed that a bispecific antibody which possessed specificity both for MHC and for CD3, both of which were expressed on T cells, was able to induce efficient proliferation of T cells whereas a mixture of the two original antibodies was unable to do this. The authors hypothesize that this synergistic effect is due to the anchoring of the T cell receptor/CD3 complex in the membrane being disturbed. In this connection, they make the assumption that the T cell receptor is unable to distinguish whether it is anchored to an antigen-presenting cell (APC) or to surface molecules within its own membrane. They therefore speculate that the T cell receptor/CD3 complex, which in vivo is triggered by antigens on another cell, reacts to changes in its mobility within the membrane.

However, the mechanism of this T cell receptor activation, which is restricted to certain T cell subpopulations, has remained unclear. The prior art has thus far assumed that this is a T cell receptor-specific effect which is probably due to the fact that, in addition to the T cell receptor, a coreceptor such as CD4 or CD8 is stimulated, with this coreceptor also generating a signal on stimulation, see Emmrich et al., Eur. J. Immunol., 18, 645 (1988).

SUMMARY OF THE INVENTION

In view of the above, an object underlying the present application is to provide a reagent which, in a general manner, restricts the stimulation of cell surface receptors to particular target cells.

According to the invention, this object is achieved by means of a multispecific reagent which possesses at least one first binding site for a cell surface receptor which requires multimeric ligand binding in order to be stimulated, and at least one second binding site for a target antigen, with the cell surface receptor and the target antigen being expressed on the same cell. The first binding site at its own does not stimulate/ the cell surface receptor, to achieve this, the second binding site has to be bound to the target antigen. By this, only such cells are selectively killed which express both, the cell surface receptor and the target antigen.

The object underlying the invention is fully achieved in this way.

Thus, the inventor of the present application has perceived that cell surface receptors which require multimeric stimulation do not imperatively have to be crosslinked by way of immobilized antibodies or, for example, antibodies which are bound by protein A or are bound to other antibodies, and that, instead, bispecific antibodies, for example, are able, in a general manner, to induce a target antigen-restricted stimulation of the cell surface receptor.

In this way, it is possible to use the target antigen to select a particular cell type and to activate the corresponding cell surface receptor on this cell type. Consequently, of the two binding sites possessed by the reagent, one is responsible for the function, namely the cell surface receptor, while the other is responsible for the specificity, namely the target antigen restriction.

According to the inventor's findings, the cell surface receptors are also, and particularly, efficiently crosslinked when the two antigens are expressed on the same cell. This result is surprising insofar as it was not clear from the prior art in what way bispecific antibodies were able to ensure a crosslinking between a function receptor and a target receptor which was sufficient to trigger the function receptor even when the two receptors were expressed on the same cell.

From a variety of his own experiments, the inventor of the present application has deduced that it is possible, in this bispecific manner, to use various target antigens, which may also, but do not have to, have a signal function, to stimulate, for example, the death receptor APO-1 or antigen-presenting cells (APCs) by way of stimulating CD40 (another member of the TNF receptor family). This was not to be expected on the basis of the studies carried out by Roosnek et al. loc. cit. And Emmrich et al. loc. cit. but, instead, required extensive experimental verification.

In view of the above, the present invention according to a further object relates to a method for treating cells in which method the novel reagent is used to bring about a target antigen-restricted stimulation of the cell surface receptor.

Thus, a further object is a method for treating cells, each cell expressing a target antigen and a death receptor, comprising the step of contacting said cells with a bispecific reagent having at least a first binding site for said death receptor and a second binding site for said target antigen, said first binding site being selected such that it stimulates the death receptor only when the second binding site has bound to the target antigen, thereby bringing about a target antigen-restricted stimulation of the death receptors of said cells.

Using this method, it is now possible, for example, to stimulate death receptors on particular target cells in order, in this way, to selectively kill cancer cells or else to, within the content of an immunosuppression, bring about the apoptotic death of activated T cells which are expressing death receptors.

Cells only expressing the death receptor but not the target antigen are not killed by the novel reagent.

The novel reagent can also be used in a pharmaceutical composition together with a pharmaceutically acceptable excipient since, according to the invention, the restriction by way of the target antigen avoids the lack of specificity which is particularly harmful when using antibodies directed against death receptors.

The methods which can be used for selecting pharmaceutically acceptable excipients, formulations, etc., are described, for example, in the patent U.S. Pat. No. 5,891,434, which was mentioned at the outset and whose disclosure is hereby made part of the subject matter of the present application.

Preference is given, in a general manner, to the novel reagent being selected from the group: multispecific, preferably bispecific antibodies or their antigen-binding fragment F(ab')$_2$; and a receptor ligand which is preferably prepared recombinantly.

The essential requirement which the novel multispecific reagent has to fulfil is that of providing two binding sites, namely one for antigen, a cell surface receptor and another one for a target antigen, with the receptor and the antigen being expressed on the same cell, and the first binding site for said cell surface receptor not stimulating said cell surface receptor at its own.

This can be brought about by specific antibodies or other antigen-binding fragments, using bispecific antibodies, trispecific antibodies or other multispecific antibodies or their antigen-binding fragments, or else by using an appropriate receptor ligand which is preferably prepared recombinantly.

The recombinant DNA technique makes it possible to synthesize different bispecific antibodies, namely tandem antibodies and diabodies. In the case of tandem antibodies, the gene fragments for two scFvs (single-chain antigen-binding proteins) are linked by way of a linker sequence and synthesized as one peptide. In the case of diabodies, two scFvs, which frequently tend to dimerize such that the variable region of the one light chain does not bind to the variable region of "its" heavy chain but, instead, to that of the second scFv molecule, without the regions being covalently linked, are expressed in one cell. In this way, it is possible to produce bispecific diabodies in which the DNA sequences for the variable regions of the light chains of the two scFv molecules to be combined are exchanged for each other in the expression vectors. After they have been synthesized, the variable regions of the antigen-specific light and heavy chains bind to each other and a recombinant antibody molecule possessing two different specificities is formed.

The fusion of different binding domains to the scFvs makes it possible to create a broad spectrum of possibilities for combining two scFvs to generate bispecific antibodies.

In a general manner, however, it can be emphasized that it is possible to use, as a reagent, any substance which binds selectively to several cell surface receptors on one cell, which means that the invention is not restricted to bispecific antibodies and bispecific receptor ligands.

In this connection, preference is given to the target antigen also being a cell surface receptor which requires multimeric ligand binding in order to be stimulated.

In this connection, it is advantageous if the target antigen is itself an activatable cell surface receptor such that the two cell surface receptors are activated and restricted simultaneously. In this way, it is possible, for example, to achieve a synergistic effect, as a result of the simultaneous stimulation of two cell surface receptors, on the cell which has thus been selected.

Preference is furthermore given to the surface receptor being selected from the group: death receptors, such as APO-1, TRAIL-R1 and TRAIL-R2; and receptors, such as CD40, which activate antigen-presenting cells (APCs).

This enumeration of the cell surface receptors is solely by way of example; the invention also includes other functional receptors which, by way of multimeric stimulation, elicit selected functions in the target cells.

Preference is furthermore given to the target antigen being selected from the group: tumor cell-specific cell surface antigen, T cell-specific cell surface antigen, CD markers generally, and cell-specific markers.

This enumeration is also solely by way of example; the invention encompasses the restriction of the multispecific reagent by any target antigens which are specific for a particular target cell.

CD markers, which characterize the different subpopulations of the leukocytes, for example, or their different development or differentiation stages, are particularly suitable for this purpose. However, the continually growing list of CD antigens also encompasses molecules which are to be found on other cell types, for example endothelial cells, nerve cells or fibroblasts; see, in this regard, Lexikon der Biologie [Encyclopedia of Biology], Spektrum Akademischer Verlag GmbH, Heidelberg, 1999, volume III, pages 323-329.

The multispecific reagent of the invention can in this way be employed universally by the function, which is stimulated by the first binding site, of the cell surface receptor being restricted by way of the target antigen.

When the cell surface receptor in the method for treating cells is a death receptor, it is then possible to induce target antigen-restricted apoptosis. This method can, for example, be employed in the immunotherapy of cancer.

Thus, when the target antigen in the new method is specifically expressed on tumor cells, it is only tumor cells which are selectively killed whereas other cells in the body which also contain the activatable cell surface receptor are not damaged since they lack the target antigen.

When, on the other hand, the target antigen is expressed specifically on T cells, it is then possible to selectively destroy the T cells which are expressing death receptors. This is advantageous, for example, in the context of immunosuppression in association with an organ transplantation.

When the target antigen is expressed specifically on antigen presenting cells, these APCs can be selectively stimulated if, in addition to the binding site for the target antigen, the multispecific reagent at least possesses a binding site for CD40.

In summary, it can be emphasized that it has for the first time become possible, as a result of the invention, to restrict the activation of particular cell surface receptors to particular target cells by using a reagent which possesses at least two binding sites, i.e. one for a cell surface receptor which is to be stimulated and a further one for a target antigen on the same cell, with this target antigen specifying the target cell.

Other advantages ensue from the description and the attached drawings.

It will of course be understood that the abovementioned features, and the features which are still to be explained below, can be used not only in the combinations which have in each case been specified but also in other combinations, or on their own, without departing from the scope of the present invention.

BRIEF DESCRIPTION OF THE DRAWINGS

Embodiments of the invention are depicted in the drawing and are described in more detail in the subsequent description.

DETAILED DESCRIPTION OF THE PREFERRED EMBODIMENT

Example 1

Binding Bispecific Antibodies to Target Cells

Figure 1:
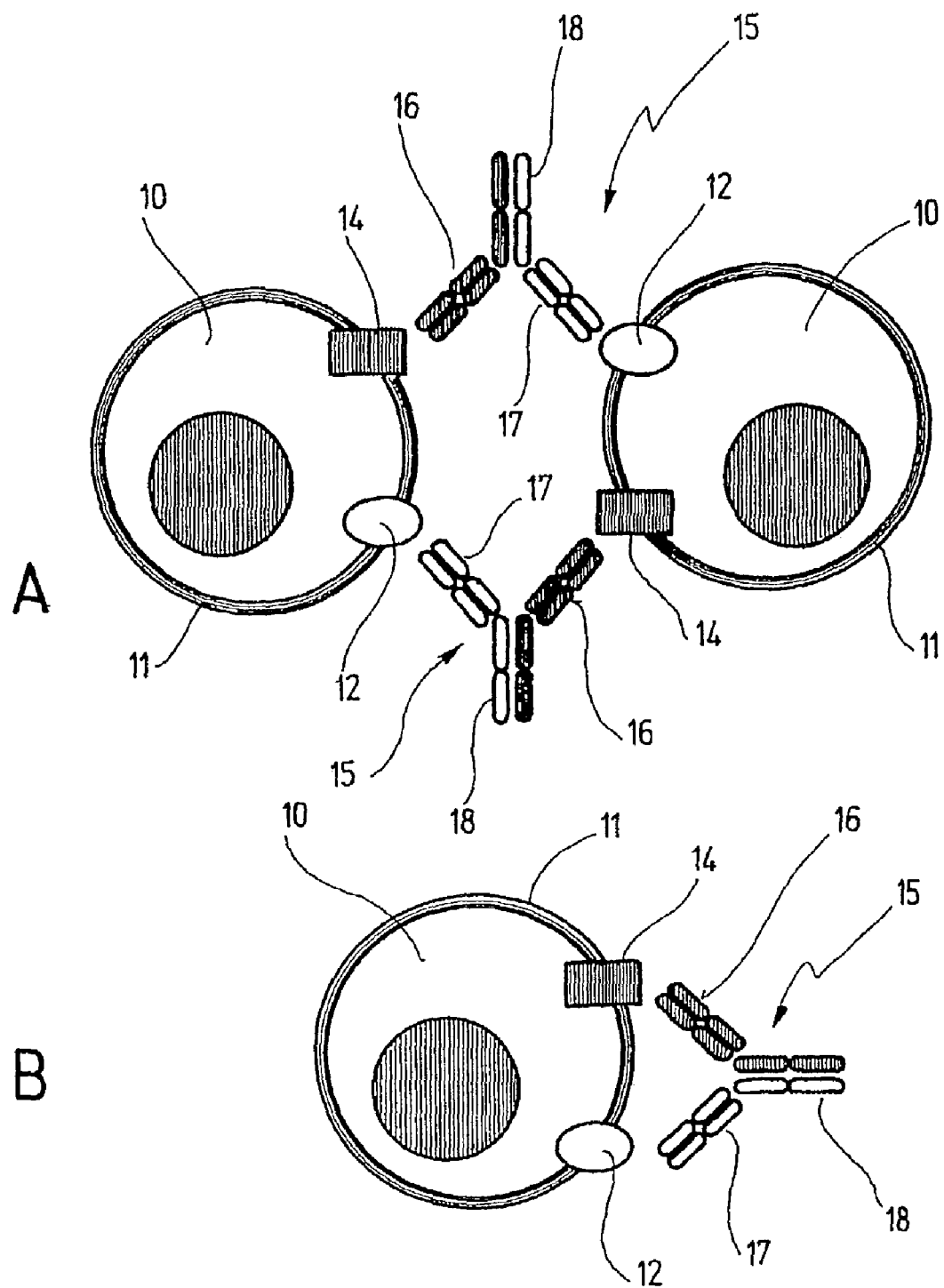
FIG. 1 shows, in diagrammatic form, the binding of bispecific antibodies to two different antigens on the same cell: A) in a bicellular manner, or B) in a monocellular manner. 10—target cell; 11—cell surface; 12—cell surface receptor; 14—target antigen; 15—bispecific antibody; 16—Fab fragment of the bispecific antibody possessing a binding site for the target antigen 14; 17—Fab fragment possessing a binding site for the cell surface receptor 12; 18—Fc fragment.

FIG. 1 depicts target cells 10 on each of whose surfaces 11 a cell surface receptor 12 and a target antigen 14 are expressed.

A bispecific antibody 15, whose Fab fragment 16 possesses a binding site for the target antigen 14 and whose Fab fragment 17 possesses a binding site for the cell surface receptor 12 binds to the target cells 10. The Fc fragment is not involved either in the binding or in a crosslinking, for which reason it was possible to use antibody fragments lacking an Fc moiety in the experiments described below. The bispecific antibody 15, which recognizes the two antigens 12 and 14, binds to both antigens on the same cell.

The cell surface receptors 12 on the target cells 10 are only stimulated when the Fab fragment 16 is simultaneously able to bind to a target antigen 14.

On the other hand, the possibility of the bispecific antibody 15 linking two target cells 10 with each other in a bicellular manner, as shown in FIG. 1A, cannot be ruled out. This means that, while, within one cell type, in which each cell 10 possesses the two antigens 12 and 14, the bispecific antibody 15 can either bind unicellularly, as in FIG. 1B, or bicellularly, as in FIG. 1A, it leads, in either case, to the target antigen restricted stimulation of the cell surface receptor 12 which is present on the same cell as the target antigen 14.

Various death receptors, such as APO-1, TRAIL-R1 or TRAIL-R2, can serve as cell surface receptor 12 while any cell surface antigens which can be used to achieve restricted stimulation of the cell surface receptor 12 can be employed as target antigen 14.

In other words, the cell surface receptor 12 is only stimulated on those target cells 10 which either carry a target antigen 14 or which, in the case of bicellular binding, are located in the immediate vicinity of such a target cell 10.

This general principle is now described below using the target antigen-restricted stimulation of the death receptor APO-1 as an example.

Example 2

Cell Lines Employed

The cell lines employed are SKW6.4 cells and Jurkat cells. SKW6.4 cells (ATCC: TIB 215) are derived from B-lymphocytes and express CD95 (APO-1) and are apoptosis-sensitive.

Jurkat cells (ATCC: TIB 152) are derived from T-lymphocytes and also express CD95 and are apoptosis-sensitive.

Both the cell lines are incubated in RPMI 1640 medium which is supplemented with 10 mM glutamate, 100 U/ml of penicillin, 100 µg/ml of streptomycin and 10% heat-inactivated fetal bovine serum (Sigma, Deisenhofen, Germany).

The APO-1 receptor (CD 95), which is expressed on both cell lines, was selected as the cell surface receptor while the CD markers CD2, CD5, CD19, CD20, CD28 and CD40 were selected as target antigens.

CD95 antibodies can be purchased from Santa Cruz Biotechnology, Santa Cruz, Calif. Monoclonal antibodies which are directed against the 6 target antigens employed can be obtained, for example, from Biotrend Chemikalien GmbH, Eupener Straße 157, Cologne.

In order to check the expression of APO-1 and the 6 target antigens, SKW6.4 and Jurkat cells were incubated, after having been incubated with the corresponding antibodies (10 µg/ml), with FITC-labeled antibodies directed against mouse IgG (Dako, Hamburg, Germany). The FACS analysis was carried out using a FACS Calibur and the CelQuest software (Becton Dickinson, San Jose Calif.).

It was found that both cell lines express APO-1 while CD20 and CD40 and, somewhat more weakly, CD19 are expressed on SKW6.4 and CD28 and, more weakly, CD2 and CDS are expressed on Jurkat cells.

Example 3

Preparing Bispecific Antibody Fragments

Bispecific antibody fragments were prepared by selectively reducing and reoxidizing disulfide bridges in the joint region; see, for example, Jung et al. loc. cit. The reaction conditions which were used were selected such that the formation of homodimers was prevented and it was possible to hybridize the modified original Fab fragments almost completely.

For the subsequent experiments, the IgG2a variant of the APO-1 antibody was hybridized with antibodies which are directed against the antigens CD19, CD20 and CD40 on SKW6.4 cells and against the antigens CD2, CDS and CD28 on Jurkat cells.

In the figures, the bispecific antibody fragments which were prepared in this way are identified by their two specificities, which are separated from each other by an X.

Example 4

Determining the Target Antigen-Restricted Induction of Apoptosis

In the experiments which were carried out, the aim was to test whether the bispecific antibody fragments were only able to stimulate the APO-1 receptor on those target cells which were also expressing the relevant target antigen for which the bispecific antibody also possessed a binding site.

This effect was determined on the basis of the rate at which the target cells were destroyed, with the target cells (SKW6.4 and Jurkat) being incubated, for this purpose, in triplicate in 96-well plates ($1 \times 10^5$/well) with 1 µg of the relevant antibody construct/mL.

After 16 hours of incubation, the viability of the remaining cells was determined using the tetrazolium salt WST-1 (Boehringer, Mannheim, Germany), which is transformed by mitochondrial enzymes and in the process forms a dark-red formazan.

The optical density was measured using an ELISA laser (Spektra-Max 340, Molecular Devices, Sunnyville, Calif.), and the percentage of cells which have been killed, with the optical density being $OD_x$, was calculated in accordance with the following formula:

$$(1-OD_x/OD_{max}) \times 100,$$

where $OD_{max}$ is the optical density which is produced by tumor cells in the absence of antibodies.

In some experiments, the percentage was determined using a chromium release test. For this purpose, target cells were incubated with $^{51}$Cr-labeled sodium chromate (80 µCi/ml, one hour), then washed thoroughly and sown in triplicate in 96-well plates. After incubating with the antibodies for 16 hours, the indicated activity was counted and the percentage of killed cells was calculated as follows:

$$cpm/cpm_{max} \times 100,$$

where $cpm_{max}$ is the radioactivity released by target cells which have been treated with a detergent.

The percentages of killed target cells which were measured using the two different methods were to a large extent in correspondence.

Example 5

Results

Figure 2:
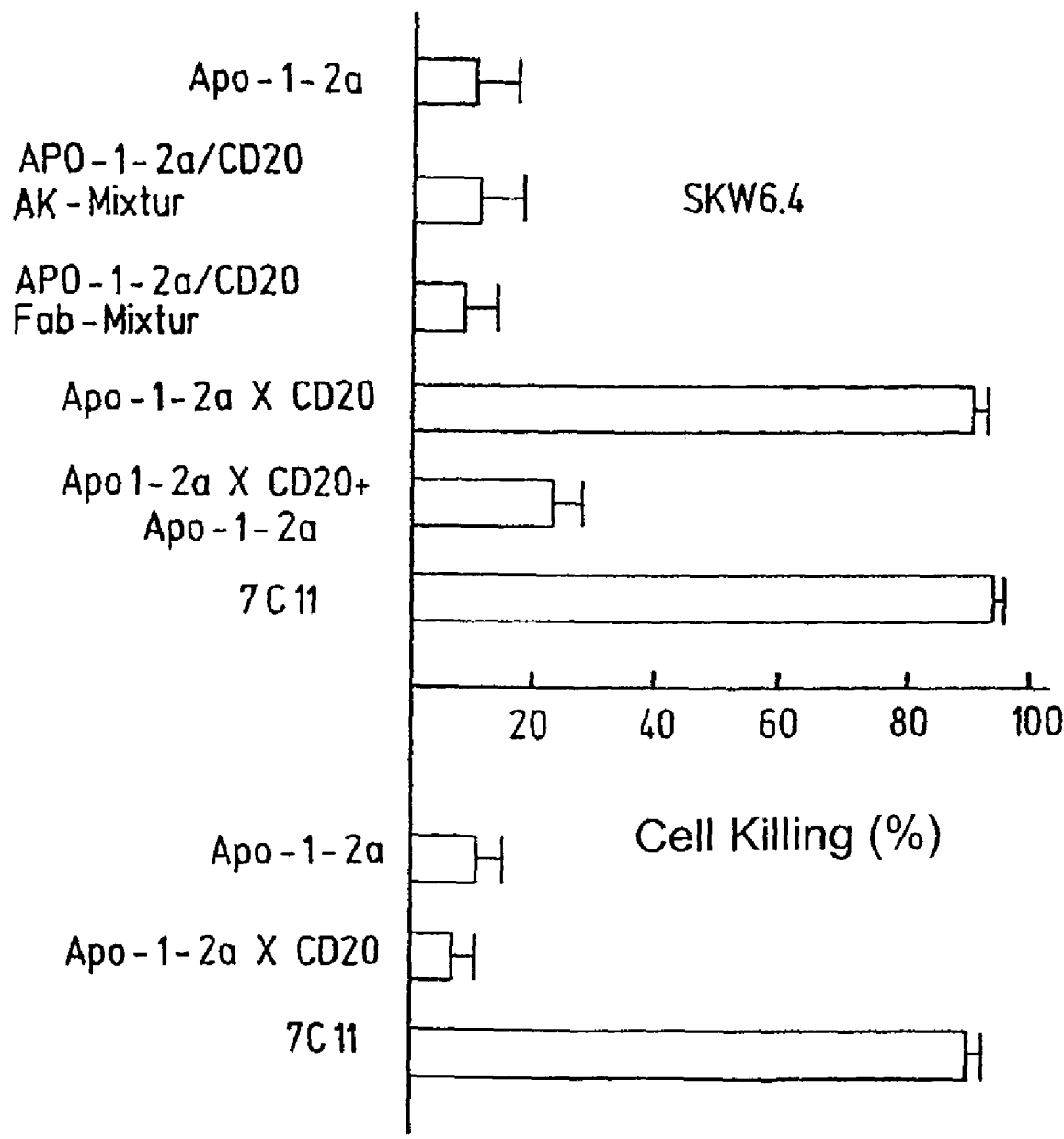
FIG. 2 shows the selective killing of SKW6.4 cells after incubating for 16 hours with a bispecific antibody fragment having a specificity for CD20 and APO-1 whereas Jurkat cells are not killed.

FIG. 2 shows that while bispecific antibody fragments having a specificity for APO-1 and CD20 (APO-1-2a×CD20) were able to kill CD20-positive SKW6.4 cells efficiently, this was not the case with the CD20-negative Jurkat cells. That both cell lines are sensitive to APO-1-mediated cell death follows from the fact that they are both killed by the antibody 7C11, which is an agonistic IgM antibody (Immunotech, Marseilles, France) which induces apoptosis.

Mixtures of the two original antibodies, which were employed either as intact antibodies or as Fab fragments, were unable to induce any apoptosis even in SKW6.4 cells.

In addition to this, coincubating the bispecific antibody fragment APO-1-2a×CD20 with the APO-1-2a antibody resulted in the lysis mediated by the bispecific antibody fragment being blocked.

Figure 3:
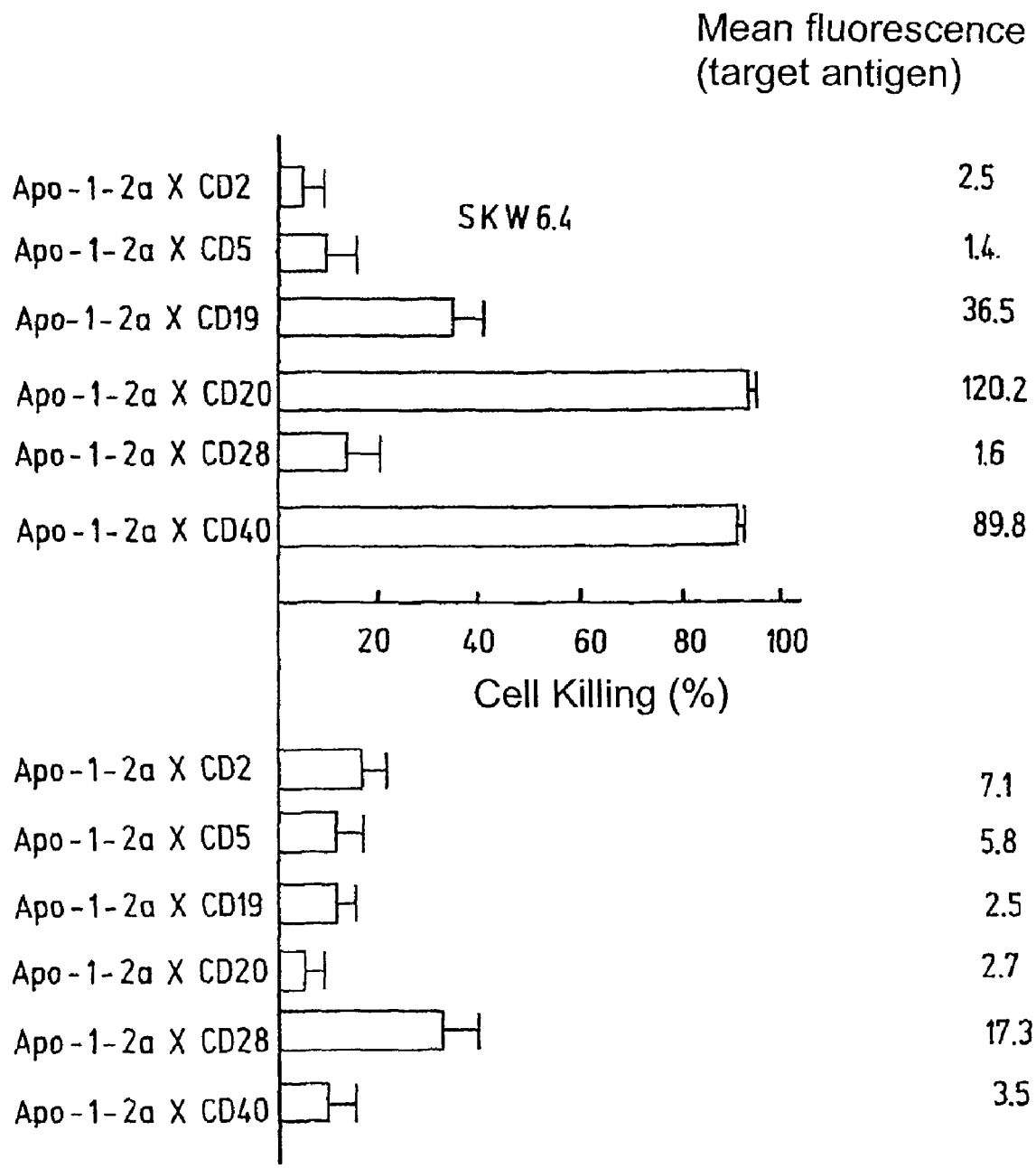
FIG. 3 shows the selective killing of SKW6.4 cells and Jurkat cells by bispecific antibodies possessing specificity for APO-1 and different target antigens.

It can be seen from FIG. 3, in which the FACS numbers on the right provide information about the expression of the relevant target antigen on the cells, that the quantity of target antigen which is expressed on the target cells is essentially responsible for the extent of the destruction of the target cells.

Significant lysis of Jurkat cells was only achieved by the APO 1-2a×CD28 construct.

APO-1-2a×CD2 only brought about marginal destruction of Jurkat cells, with APO-1-2a×CD5 in fact being completely ineffective with these cells. On the other hand, APO-1-2a× CD20 and APO-1-2a×CD40 were very efficient, bringing about virtually 100% destruction of SRW6.4 cells.

APO-1-2a×CD19 and APO-1-2a×CD28 were less effective on SKW6.4 cells and Jurkat cells, respectively.

On the basis of these results, it can be stated that apoptosis was only induced in cells which were expressing the appropriate target antigen in addition to the APO-1 receptor.

What is claimed is:

1. A bispecific antibody fragment which is lacking an Fc moiety, wherein the antibody fragment has a monovalent binding site for a death receptor and a binding site for a target antigen, wherein the death receptor is APO-1 and the target antigen is CD20.

2. A pharmaceutical composition comprising the bispecific antibody fragment of claim 1.

* * * * *